United States Patent [19]

Cares

[11] 4,045,370

[45] Aug. 30, 1977

[54] CATALYST FOR THE DEPOLYMERIZATION OF LOWER POLYMERS OF ISOBUTENE

[75] Inventor: William Ronald Cares, Houston, Tex.

[73] Assignee: Petro-Tex Chemical Corporation, Houston, Tex.

[21] Appl. No.: 664,901

[22] Filed: Mar. 8, 1976

[51] Int. Cl.$^2$ .......................... B01J 21/08; B01J 23/30
[52] U.S. Cl. .............................. 252/458; 260/683 PD
[58] Field of Search ................ 260/683 PD; 252/458, 252/467

[56] References Cited

U.S. PATENT DOCUMENTS 3,365,513   1/1968   Heckelsberg ........................ 260/683

*Primary Examiner*—W. J. Shine
*Attorney, Agent, or Firm*—Kenneth H. Johnson

[57] ABSTRACT

Oligomers of isobutene are depolymerized at 200° to 580° C in vapor phase by contact with a catalyst consisting essentially of the oxide of Cr, Mo or W on a high surface area silica support.

1 Claim, No Drawings

CATALYST FOR THE DEPOLYMERIZATION OF LOWER POLYMERS OF ISOBUTENE

BACKGROUND OF THE INVENTION

The present invention relates to an improvement in depolymerizing olefin polymers and more specifically the depolymerization of polymers of isobutene.

The polymers of particular interest in the present invention are the lower polymers or oligomers of isobutene. Frequently the polymers are formed unintentionally in the recovery and purification of isobutene monomer. For example, the sulfuric acid extraction of isobutene from hydrocarbon streams usually results in oligomers comprised of principally dimers, trimers and tetramers.

The isobutene monomer may be more valuable compared to the oligomers because of its wide utilization, e.g., polymerization. The lower polymers, oligomers, have found some degree of utilization as gasoline octane improvers, and the dimers are employed as raw materials for detergent intermediates, antioxidants, lube oil additives and the oxo and Koch reactions. Thus a successful depolymerization need not reduce all of the oligomer or oligomers to isobutene, especially if the principal residual oligomer is diisobutene.

In the past isobutene polymers have been depolymerized by heating the polymers in an externally heated tube (thermal degradation) or contacting the heated polymers with various catalysts such as attapulgite clay or silicamagnesia (catalytic degradation).

The present invention relates to the latter general type of depolymerization, using a novel catalyst, which provides the advantages of depolymerization of the various oligomers to high yields of isobutene monomer and high secondary selectivity to diisobutene. Another advantage is the substantial absence of catalyst coking or the formation of high molecular weight non-volatile products. These and other advantages will become obvious from the following description and explanation of the invention.

SUMMARY OF THE INVENTION

Briefly stated the present invention lies in the catalyst and the process of using said catalyst to depolymerize polyolefins. The catalyst consist essentially of Periodic Table Group VI B metal oxides. A particular aspect of the present invention is a process for the depolymerization of olefin polymers comprising contacting said olefin polymers in vapor phase with a catalyst consisting essentially of an oxide of chromium, molybdenum, tungsten or mixture thereof on a substantially inert solid support and recovering monomer or lower polymers corresponding to the repeating units of said olefin polymers.

The preferred polyolefins are preferably low polymers, generally described as oligomers which are polymers of from two to four or five repeating monomer units, although the number of repeated units may be higher, for example, up to ten repeated monomer units.

The present process has been found to be particularly useful for depolymerizing oligomers of isobutene which comprise which comprise essentially dimers, trimers and/or tetramers. These materials are gaseous under the conditions of the depolymerization reaction.

DETAILED DESCRIPTION OF THE INVENTION

The depolymerizations are carried out in vapor phase. The oligomers are usually liquid or viscous materials at room temperatures (25° C) and are vaporized by any conventional means to be fed through the reactor and catalyst. Generally temperatures in the range of 200° to 580° C are suitable with temperatures in the range of 300° to 500° C being more preferable for carrying out the depolymerizations. In many instances the feed to the depolymerization is composed of a mixture of oligomers, and in that case or in the case of higher oligomers, such as trimers and tetramers temperatures in the upper portion of the range, e.g., 460° to 580° C favor complete depolymerization to isobutene, while temperatures in the lower region of the temperature range, e.g., 300° to 460° C result in a larger proportion of dimer in the product, although the isobutene is still a principle product.

The process may be operated at atmospheric pressure, although superatmospheric conditions may be advantageous when it is desirable to recover the depolymerization products (especially the monomer) in liquid state.

Pressure of up to at least 150 psig are particularly contemplated. Under elevated pressure conditions the monomer products, e.g., butenes are recovered in the liquid state by cooling to ordinary temperatures, e.g., 20° to 60° C.

Hence, it is apparent that those of skill in the art will select the specific conditions within the ranges specified in regard to the nature of the feed to the depolymerization reaction and the desirable distribution of depolymerized material in the product. Only a minimal amount of optimization would be required to achieve this.

The metal oxide is selected from the oxides of chromium, molybdenum or tungsten. Tungsten is the preferred metal. The metal is used in the form of an oxide. In the case of these three metals there are many oxides possible, e.g., $CrO$, $CrO_2$, $Cr_2O_3$, $MoO_2$, $MoO_5$, $Mo_2O_3$, $WO_3$, $W_2O_5$ and $WO_2$. All of the oxide forms are active as such and it is contemplated that one or a mixture of the oxides of one or a mixture of Cr, Mo or W may be employed.

The support may be any of those materials normally used such as alumina, silica, fire brick, glass beads, ceramics and the like. However, a preferred group of support materials comprise silica, for example, high surface area silicas or fumed silica. Even more preferable are silica gels having high surface area.

The high surface area support is defined as a support material having over 50 square meters per gram, preferably over 70 square meters per gram.

Normally from 0.01 to 95 preferably 0.1 to 35 and more preferably 1 to 25 weight percent of the Cr, Mo or W oxide will be deposited on the support based on the total weight of support and Cr, Mo or W oxide. The chromium, molybdenum or tungsten oxides, may also be employed without a support, i.e., in substantially pure form, for example, pelleted tungsten oxide.

The oxides may be deposited on silica gel or other solid support, as such or in the form of compounds which decompose on heating, for example, before the reaction or in the reaction to produce oxides. Preferably the decomposition products other than the metal oxide are of a volatile nature and are removed by heating, or the precursors, such as $H_4SiW_{12}O_{40}$ may form silica residues. Some other suitable precursors are tungstic acid, molybdenum hydroxide, molybdenum trioxyhexachloride, silicomolybdic acid, chromium III sulfite, chromium carbonyl and the like.

The reactant stream may comprise substantially oligomer, e.g., over 90 weight percent or the stream may be diluted with solvents or inert diluents, for example, propylene, n-butane, n-butenes or isobutene. Preferably the feed to the depolymerization catalyst will consist essentially of the oligomers in a vaporized state, and in this condition LHSV's of 0.8 to 7.5 are suitable.

EXAMPLES

Two continuous flow, quartz reactors were used in the examples. Reactor A: Ten ml of the prepared catalyst was supported in and slightly above a 10 mm restricted section of a 30 mm OD reactor with pyrex glass beads used above and below the catalyst bed as bed support and as a reactant preheat section. Reactor B: A second reactor of uniform 30 mm OD quartz was loaded with 75 ml of the catalyst, again using pyrex glass beads as bed support and preheat sections; the minimal length of the preheat section of this reactor resulted in a low preheat efficiency. Both reactors contained a central thermocouple well which allowed monitoring of the temperature at the top of the 10 ml catalyst charge and along the axial length of the 75 ml catalyst charge.

The catalyst was prepared by the addition of Davison Grade 59* silica gel, 3-8 mesh, to an aqueous solution of $H_4SiW_{12}O_{40}$ hydrate, followed by evaporation of the mixture to dryness. The active catalyst concentration was 15.0 weight percent as $WO_3$ of the total weight of catalyst and support.

*Product of W. R. Grace and Co., Davison Chemical Division, a silica gel having particle size 3-8 mesh (Tyler Sieve) bulk density 25.0 lbs/cu. ft., total volatile at 1,750° F. (max.) 3.5% surface area 340 sq. meters/grams, pore volume 1.15 cc/gram.

Feed was supplied to the 10-ml catalyst reactor by a syringe pump and to the 75-ml reactor by a Lapp pump; feeds were introduced to the top of the reactor, through hypodermic needles, as room temperature liquids.

Product analyses were by gas chromatography; liquid products were identified as isobutene dimer, trimer or tetramer with no attempt made to differentiate among the various isomers of each. Gas phase products were separated to the individual $C_1$ through $C_4$ (and some $C_5$) species.

EXAMPLE 1

REACTOR A

Table I gives the operating parameters and analyses of liquid products for the various runs over the 10-ml catalyst bed and Table II gives the analyses for the gas phase products from four of these runs. The runs of Table I are presented in real time sequence over the catalyst; the caralyst for the first four runs was air oxidized, followed by $H_2$ reduction to the blue form and had previously been used for a number of tert-butanol dehydration experiments. Before the 5th run of Table I the catalyst was reoxidized with air to the yellow $WO_3$ form; before the 8th run the catalyst was again air reoxidized to the $WO_3$ form followed by $H_2$ reduction to the blue form. No further oxidation or reduction treatments were given to the catalyst for the remainder of the runs. It should be noted that the oxidized form of the catalyst is reduced by the reactants and that by the 7th run the catalyst had returned to its reduced state.

The feed is specified in Table I preceeding the runs in which the feed was employed. The product is described as gas phase and liquid phase. The gas phase is predominately isobutene which is shown in the representative gas phase analyses of Runs 6, 8, 9 and 10 of Example 1 (Table II).

TABLE I

| Run | Reaction Temp.,° C | LHSV | Wt. % Feed to Gas Phase Products[1] | Wt. % Feed to Liquid Phase Products | Liquid Product Analysis Weight Percent | | |
|---|---|---|---|---|---|---|---|
| | | | | | Dimer | Trimer | Tetramer |
| (Feed in Runs 1-8: isobutene polymer, wt. %: Dimer 73.8%, Trimer 24.9%, Tetramer 1.4%) | | | | | | | |
| 1 | 312 | 2.5 | 19.6 | 80.4 | 92.4 | 7.6 | — |
| 2 | 312-446 | 2.5 | 51.0 | 48.0 | 88.7 | 11.1 | 0.2 |
| 3 | 446 | 2.5 | 51.7 | 48.3 | 87.9 | 12.1 | 0.0 |
| 4 | 455 | 1.5 | 58.9 | 41.1 | 91.4 | 8.5+ | 0.1 |
| 5 | 452 | 1.5 | 58.9 | 41.1 | 94.9 | 2.1 | 3.0 |
| 6 | 452 | 1.5 | 68.7 | 31.3 | 95.3 | 2.2 | 2.6 |
| 7 | 451 | 2.7 | 74.4 | 25.6 | 94.0 | 5.4 | 0.6 |
| 8 | 357 | 2.5 | 55.4 | 44.6 | 93.9 | 6.1 | 0.0 |
| (Feed Runs 9 and 10: isobutene polymer, wt. %: Dimer 0.4%, Trimer 99.6%, Tetramer 0.0%) | | | | | | | |
| 9 | 355 | 2.5 | 40.6 | 59.4 | 58.0 | 42.0 | 0.0 |
| 10 | 404 | 2.5 | 46.9 | 53.1 | 56.1 | 43.9 | 0.0 |
| (Feed Runs 11-14: isobutene polymer, wt. %: Dimer 99.8%, Trimer 0.2%, Tetramer 0.0%) | | | | | | | |
| 11 | 308 | 2.6 | 30.9 | 69.1 | 98.4 | 1.6 | 0.0 |
| 12 | 308-352 | 2.6 | 43.6 | 56.4 | 99.2 | 0.8 | 0.0 |
| 13 | 360 | 2.6 | 37.0 | 63.0 | 99.6 | 0.4 | 0.0 |
| 14 | 421 | 2.6 | 49.8 | 50.2 | 99.8 | 0.2 | 0.0 |

[1]Analysis for runs 6, 8, 9 and 10 reported in Table II

TABLE II

| GAS PHASE ANALYSES, WEIGHT PERCENT | | | | |
|---|---|---|---|---|
| Run | 6 | 8 | 9 | 10 |
| $CO_2$ | — | — | — | — |
| $C_3H_8$ | — | — | trace | 0.0+ |
| $C_3H_6$ | — | 0.4 | 0.3 | 0.6 |
| isobutane | 1.1 | 0.2 | 0.2 | 0.3 |
| n-butane | 0.3 | 0.1 | trace | 0.0 |
| 1-butene | 0.6 | 0.4 | 0.0+ | 0.1 |
| isobutene | 95.7 | 97.7 | 99.4 | 98.6 |
| trans-2-butene | 1.3 | 0.8 | 0.1 | 0.1 |
| cis-2-butene | 0.9 | 0.5 | 0.1 | 0.1 |
| Butadiene | — | — | — | — |
| Weight Percent Distribution of Butenes Only | | | | |
| 1-butene | 0.6 | 0.4 | 0.0+ | 0.1 |
| trans-2-$C_4H_8$ | 1.4 | 0.8 | 0.1 | 0.1 |
| cis-2-$C_4H_8$ | 0.9 | 0.5 | 0.1 | 0.1 |
| isobutene | 97.1 | 98.4 | 99.8 | 99.7 |

EXAMPLE 2

REACTOR B

The catalyst as described had been used previously for depolymerization. It was air oxidized and reduced with $H_2$ (oxidized form, yellow, reduced form, blue and a feed of isobutene polymer, wt. %: dimer 28.8%, trimer 67.3%, tetramer 3.9% was initiated. The results and operating conditions are set out in Table III for a continuous run of 120 minutes For the entire run the weight % of feed recovered as (1) room temperature liquid product was 21.4 wt. % and (2) gas phase product (assuming the analysis in Table IV was constant for the entire run) is 72.5 wt. % which on material balance accounts for 93.8 wt. % of the feed.

TABLE III

| Minutes On Stream | Mid-Point Bed Temp., °C | LHSV | Wt. % Feed Recovered As Liquid Product | Liquid Product Analysis[1] Weight Percent | | |
|---|---|---|---|---|---|---|
| | | | | Dimer | Trimer | Tetramer |
| 30 | 430± 30 | 3.2 | 13.9 | 90.5+ | 8.9 | 0.6 |
| 60 | 435 | 3.2 | 20.5− | 89.4 | 9.4 | 1.2 |
| 90 | 442 | 3.2 | 24.9 | 90.5+ | 8.3 | 1.1 |
| 120 | 430 {340 top, 582 btm.} | 3.2 | 26.2 | 78.2 | 21.1 | 0.8 |

[1]Analysis of gas phase at 42 minutes on stream reported in Table IV

TABLE IV

GAS PHASE ANALYSES, WEIGHT PERCENT AT 42 MINUTES OF OPERATION IN 75 ML REACTOR

| Component | 42 Minutes On Stream |
|---|---|
| $CH_4$ | 1.4 |
| $C_2H_6$ | 0.7 |
| $C_2H_4$ | 0.8 |
| $CO_2$ | ≦trace |
| $C_3H_8$ | 1.2 |
| $C_3H_6$ | 5.4 |
| isobutane | 1.9 |
| n-butane | 0.0+ |
| 1-butene | 0.7 |
| isobutene | 80.1 |
| trans-2-butene | 0.8 |
| cis-2-butene | 0.7 |
| Butadiene | 0.2 |
| Unknown | 0.4 |
| Unknown } Probably $C_5H_{10}$'s | 2.0 |
| Unknown } | 3.0 |
| Unknown | 0.6 |

| Weight Percent Distributions of Butenes Only | |
|---|---|
| $1\text{-}C_4H_8$ | 0.9 |
| $trans\text{-}2\text{-}C_4H_8$ | 1.0 |
| $cis\text{-}2\text{-}C_4H_8$ | 0.9 |
| $iso\text{-}C_4H_8$ | 97.3 |

The invention claimed is:

1. A catalyst composition for the depolymerization of olefin polymers consisting essentially of an oxide of tungsten on a silica support having a surface area over 50 square meters per gram prepared by the process of mixing an aqueous solution of $H_4SiW_{12}O_{40}$ onto a silica gel and drying the mixture.

* * * * *